ized Patent [19] [11] 3,936,636
Percival [45] Feb. 3, 1976

[54] METHOD OF PRODUCING A REPRESENTATION OF A PLANAR SECTION OF A BODY USING SCANNING RADIOLOGY

[75] Inventor: William Spencer Percival, London, England

[73] Assignee: EMI Limited, Hayes, England

[22] Filed: Mar. 27, 1974

[21] Appl. No.: 455,394

[30] Foreign Application Priority Data
Apr. 7, 1973 United Kingdom............... 16783/73

[52] U.S. Cl. ................. 250/336; 250/362; 250/369
[51] Int. Cl.² ........................................... G01T 1/16
[58] Field of Search ............ 250/336, 362, 366, 369

[56] References Cited
UNITED STATES PATENTS
3,778,614 12/1973 Hounsfield.......................... 250/362

Primary Examiner—Davis L. Willis
Attorney, Agent, or Firm—Fleit & Jacobson

[57] ABSTRACT

In radiological apparatus, edge values derived by monitoring the radiation passed through a body along many co-planar paths are subjected to a transformation process, such as a convolution integral or Fourier transform process, in order to evaluate the absorption or transmission coefficients of the elements of a matrix of elements notionally delineated, in the plane of the paths, in the body. The values are inversely transformed to synthesize further edge values, and corresponding ones of the first mentioned and further edge values are compared to derive edge value error signals. The edge value error signals are indicative of errors in the evaluation of said coefficients and they are subjected to the aforementioned transformation process to derive therefrom individual correction signals for the various elements of the matrix.

3 Claims, 1 Drawing Figure

U.S. Patent   February 3, 1976   3,936,636
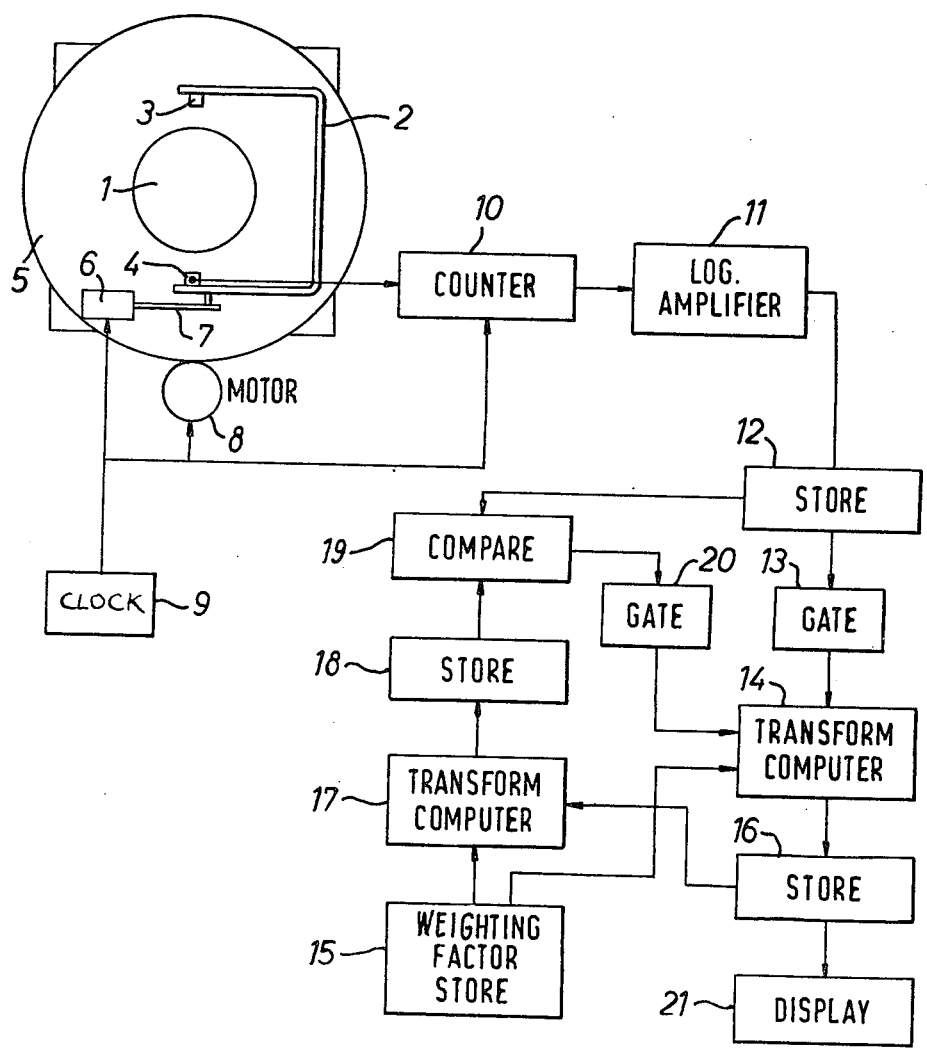

METHOD OF PRODUCING A REPRESENTATION OF A PLANAR SECTION OF A BODY USING SCANNING RADIOLOGY

This invention relates to radiology. In particular, it relates to a method of producing a representation of the absorption of elements of a planar section of a body in response to examination of the body by means of penetrating radiation, such as X- or γ- radiation.

It has been proposed hitherto to form a radiograph of a planar, cross-sectional region of a body by passing a narrow sweep of X- or γ- rays transversely through said region in a series of different directions and measuring the absorption of the rays in order that the absorption coefficients of a matrix of elements notionally delineated in said region may be computed. Our U.S. Pat. No. 3,778,614 discloses a method and apparatus for providing a representation of the absorption coefficients of a matrix of such notional elements by a process of successive approximations. The sweep of rays from a source of radiation is directed in a precisely determined manner through the region towards detecting means; the cross section of each ray being small with respect to the transverse extent of the body in said plane. It will be apparent that the relationship between the source output and the radiation detected by the detecting means is indicative of the absorption suffered by the radiation in traversing the elements in a ray path, and thus an approximate absorption coefficient value may be assigned to each element by assigning substantially the same amount of absorption to each element. By passing rays through the body to provide a unique group of ray paths intersecting each element, the value of absorption coefficient assigned to each element may be altered in accordance with a sequential process of successive approximations, by which the individual values assigned to each element tend to converge on the actual value thereof. The individual values of absorption coefficient assigned to each element are called mesh values in this specification.

The various over-all absorption values measured along respective paths (which values, in this specification, will be referred to as "edge values"), may alternatively be directly transformed by transformation processes, such as Fourier transforms or convolution integral processes, for example, in order to evaluate the absorption coefficient of each element, that is each mesh value. Such processes are described in the Article entitled "Representation of a Function by Its Line Integrals, with Some Radiological Applications," by A. M. Cormack, published in the Journal of Applied Physics, September 1963, Volume 34, No. 9 and October 1964, Volume 35, No. 10, and in the Article entitled "Three-dimensional Reconstruction from Radiographs and Electron Mictrographs : Application of Convolutions instead of Fourier Transforms" by G. N. Ramachandran and A. V. Lakshminarayanan, published in the Proceedings of the National Academy of Science, U.S.A. September 1971, Volume 68, No. 9. Such transformation processes give good resolution of the absorption coefficients, but have the disadvantage that, unlike the process of successive approximations described in our aforementioned Specification there occurs no self-correction of the evaluated coefficients, with respect to low-frequency spatial variations in absorption coefficients across the matrix, or with respect to an over-all d.c. offset of said coefficients relative to a datum level.

It is an object of the invention to provide an improved method of producing a representation of the absorption of elements in a planar section of a body in response to an examination of the interior of a body, by means of scanning radiology which combines the advantages of transformation processes and processes of successive approximation.

According to the present invention from one aspect there is provided a method of producing a representation of the absorption of elements in a planar section of a body in response to an examination of the a body with penetrating radiation such as X- or γ- radiation including the steps of:

i. deriving a respective edge value indicative of the absorption suffered by said radiation on traversing each of a plurality of substantially co-planar paths of which at least some intersect, the cross sectional dimensions of each ray being small compared with the dimensions of the body, ii. performing a transformation process upon said edge values to provide mesh signals indicative of a first estimate of the values of the coefficient of radiation absorption or transmission of respective ones of a plurality of elements in a matrix of elements notionally delineated in said body in the plane of said paths, and iii. operating upon said mesh signals by:
  a. deriving, from said mesh signals, further edge values indicative of the values which respective ones of said first mentioned edge values should assume if the said mesh signals are correct,
  b. comparing said first edge values with respective ones of said further edge values to derive edge error signals,
  c. transforming said edge error signals to mesh error signals indicative of errors in said mesh signals, and
  d. changing said mesh signals in accordance with said mesh error signals.

In one example of the invention, a plurality of edge values may be measured around a body to be examined in the manner described in said Patent Specification. The edge values are then transformed according to a predetermined transformation process, such as a convolution integral or Fourier transform or inverted process as described in the aforesaid articles, to provide mesh signals indicative of the absorption coefficients of respective ones of a plurality of elements in a matrix of notional elements in the plane of the body examined by the radiation. These mesh signals are stored, for example in the storage means of an electronic computer.

According to this invention, the mesh signals are subjected to a corrective operation. The mesh signals are applied to means for performing a transformation which is the inverse of the transformation process referred to above. Such a re-inversion process may simply be performed by summing the values of mesh signals assigned to elements in each path (taking suitable account of the fact that the paths will not intersect all of the elements equally, in general, so that weighting factors have to be applied in the manner described in the aforementioned Patent Specification) so as to derive further edge values which are indicative of what the first-mentioned edge values should have been if the mesh signals were all correct. Ideally, therefore comparison of the further edge values with the corresponding first mentioned edge values should yield a zero result. However in practice such comparison yields an edge error signal indicative of errors which may have been produced in the transformation processing. It will thus be apparent that an edge error signal ($\Delta Z$) may be produced for each edge value by comparing the value of each of the further edge signals with the corresponding one of the first mentioned edge values, for example by subtraction i.e.

$$\Delta Z = Z_c - Z_c',$$

where $Z_c$ represents one of the first-mentioned edge readings (i.e. a reading actually measured) and $Z_c'$ represents the corresponding one of the further edge readings (which is not actually measured but is synthesized from the aforementioned mesh signals for elements disposed along the respective path).

The plurality of edge error signals thus produced are consequently transformed in a similar manner to the first mentioned edge readings (i.e. by the aforementioned transformation process) to provide mesh error signals indicative of the error in the stored value of each cell signal. Thus, by changing the mesh signals in accordance with their respective mesh error signals, the error therein is reduced.

In order that the invention may be fully understood and readily carried into effect, it will now be described by way of example with reference to the single FIGURE of the accompanying drawing which shows in block diagrammatic form an example of apparatus for carry out the method according to the invention.

The apparatus illustrated is arranged to examine a planar section of a body placed in aperture 1. A frame member 2 locates a source of said penetrating radiation, for example a Coolidge tube 3, opposite to a radiation detector 4 which may for example comprise a NaI scintillator crystal and associated photomultiplier tube. The frame 2 is capable of performing a reciprocating motion relative to a discoidal backplate 5, being driven by a reciprocating motor 6 and a connecting rod 7. In the position shown, the frame 2 may oscillate in a right-left-right direction. The backplate 5 is capable of being rotated about the aperture 1, in the plane of reciprocation of frame 2, by motor 8. Thus the X-ray tube 3 may be arranged to pass a sweep of parallel rays through a body placed in aperture 1, from a series of different angles. The reciprocating motor 6 and motor 8 operate in response to pulses from a clock 9 such that the absorption of radiation along a predetermined sequence of co-planar rays through the body may be determined. The output pulses from the detector 4 are counted in a counter 10 and read out in response to pulses from clock 9.

It will be apparent that the digital numbers derived from counter 10 are indicative of the aforementioned edge values, and signals indicative of said edge values are applied to a logarithmic amplifier 11 to provide output signals respectively indicative of the absorption or transmisssion of radiation along the ray paths, and which are stored in store 12. The signals stored in store 12 indicative of said edge values, are applied via gate 13 to a transform computer 14, which is arranged to effect a transformation process to transform said signals indicative of edge values to mesh signals, respectively indicative of the absorption or transmission coefficients of a plurality of elements in a matrix of elements notionally delineated in the plane section of the body described by the locus of rays from said X-ray source. The computer may perform the transformation process by a Fourier transformation as described in the first aforementioned articles or by a convolution transformation as described in the section of the aforementioned article.

To compensate for variation in the absorption for various angles at which different rays pass through the elements of the matrix, various weighting values are assigned (as aforementioned) to the edge values for the transformation computation, the weighting factors being derived from a weighting factor store 15, and the values thereof being assigned as described in the aforementioned Patent Specification. The mesh values derived from the computations are stored in a store 16, there being one mesh value for each element or mesh of the matrix notionally delineated in the planar section of the body examined by the radiation, each mesh value being stored in a respective storage location. The computer 14 thus carries out the well-known mathematical operation on inversion that is it transforms or inverts edge values into mesh values.

Another transform computer 17 is provided for transforming the stored mesh signals to signals indicative of further edge values, by performing a transformation which is the inverse of that performed by computer 14. Thus it re-inverts the mesh value signals. Since the mesh signals are indicative of the absorption coefficients, the mesh signals assigned to elements in the paths of respective rays are summed to derive said further edge values indicative (in logarithmic form) of what the original edge values should have been if the mesh signals as stored in store 16 were correct. Each of the mesh signals in the summations is weighted by similar weighting factors to those applied to computer 14 from store 15, and the further edge values thus derived from the computer 17 are stored in a store 18. Comparator 19 provides edge error signals indicative of the difference between a set of signals indicative of the original (i.e. measured) edge values derived from store 12, and respective ones of a corresponding set of further edge values derived from store 18, said edge error signals being applied to the transform computer 14 via gate 20.

In operation, the X-ray source 3 and detector 4 are arranged to measure the absorption along a plurality of parallel sets of ray paths at different angles through a section of the body to thereby generate a collection of signals indicative of edge values which are stored in store 12. Gate 13 is triggered open and the transform computer 14 generates a set of mesh signals from the edge signals which are stored in store 16.

To reduce errors produced in this transformation, a corrective calculation is then performed. From the mesh values, transform computer 17 generates a corresponding set of further edge signals which are stored in store 18. Comparator 19 subtracts the signals indicative of edge values from the corresponding ones of said further edge values. These edge value signals may be derived from store 12 or directly from amplifier 11 if a further set of edge value measurements is taken. Gate 20 is opened and gate 13 is shut, and edge error signals from the comparator 19 are applied to transform computer 14. The transform of said edge error signals comprises mesh error signals indicative of errors in the mesh signals stored in store 16. Information in the store 16 is thus changed, in this example by adding the mesh error signals to corresponding ones of said stored mesh signals to update the store 16.

It will be apparent that a series of such corrective calculations may be performed so that the mesh signals converge and become indicative of the actual value of the absorption or transmission coefficients of the elements of the matrix. A threshold may be included in the system to stop the corrective calculations when either the edge error signals or the transforms thereof reach a certain value indicating a required accuracy in the cell signals.

The contents of store 16, may be then displayed on a display 21 which may comprise, for example, a cathode ray tube means or a tone printer.

Although the method according to the invention requires more processing time than is required for a single transformation process, the accuracy of the initial transformation can be reduced, reducing the required calculation complexity as compared with the accuracy of transformation which would have been required had the transformation process been used alone. Moreover there is no need to increase the number of edge readings and hence the radiation dosage applied to the body, which may be living matter, is not increased.

Although the transformation of the edge values in accordance with the invention may be carried utilising any suitable transformation process, the transformation which achieves the transposition of said edge values to said corresponding mesh signals may be performed according to the disclosure in co-pending British Pat. application No. 19528/73, corresponding to U.S.A. application, Ser. No. 462,104.

What I claim is:

1. A method of producing a representation of the absorption of elements in a planar section of a body in response to an examination of the body with penetrating radiation such as X- or γ- radiation including the steps of:
   i. deriving a respective edge value indicative of the absorption suffered by said radiation on traversing each of a plurality of substantially co-planar paths of which at least some intersect, the cross sectional dimensions of each ray being small compared with the dimensions of the body,
   ii. performing a transformation process upon said edge values to provide mesh signals indicative of a first estimate of the values of the coefficient of radiation absorption of respective ones of a plurality of elements in a matrix of elements notionally delineated in said body in the plane of said paths, and
   iii. operating upon said mesh signals by:
   a. deriving, from said mesh signals, further edge values indicative of the values which respective ones of said first mentioned edge values should assume if the said mesh signals are correct,
   b. comparing said first edge values with respective ones of said further edge values to derive edge error signals,
   c. transforming said edge error signals to mesh error signals indicative of errors in said mesh signals, and
   d. changing said mesh signals in accordance with said mesh error signals.

2. A method according to claim 1 wherein said transformation process is an integral convolution process.

3. A method according to claim 1 wherein the transformation of said edge error signals into mesh error signals is effected in accordance with the same transformation process used to provide said mesh signals from said edge values.

\* \* \* \* \*